(12) United States Patent
Yang et al.

(10) Patent No.: US 7,957,782 B2
(45) Date of Patent: Jun. 7, 2011

(54) BINDING STRAP USED IN CONNECTION WITH SPO2 SENSOR

(75) Inventors: Xingbao Yang, Shenzhan (CN); Jianfang Cao, Shenzhan (CN); Jilun Ye, Shenzhan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1305 days.

(21) Appl. No.: 11/517,794

(22) Filed: Sep. 8, 2006

(65) Prior Publication Data

US 2007/0270676 A1 Nov. 22, 2007

(30) Foreign Application Priority Data

May 20, 2006 (CN) .................. 2006 2 0059373 U
May 20, 2006 (CN) .................. 2006 2 0059374 U

(51) Int. Cl.
*A61B 5/1455* (2006.01)
(52) U.S. Cl. ........................ 600/344; 600/310
(58) Field of Classification Search .................. 600/344; 24/16
See application file for complete search history.

(56) References Cited

U.S. PATENT DOCUMENTS 5,054,488 A * 10/1991 Muz .............................. 600/344
5,247,931 A * 9/1993 Norwood ..................... 600/344
5,687,455 A * 11/1997 Alexander .................. 24/16 PB
5,879,292 A 3/1999 Sternberg et al.
5,991,648 A * 11/1999 Levin ............................. 600/344
7,657,294 B2 * 2/2010 Eghbal et al. .................. 600/344

FOREIGN PATENT DOCUMENTS

CN 2054687 U 3/1990
CN 2306025 Y 2/1999

* cited by examiner

*Primary Examiner* — Eric F Winakur
*Assistant Examiner* — Marjan Fardanesh
(74) *Attorney, Agent, or Firm* — Kory D. Christensen; Stoel Rives LLP

(57) ABSTRACT

A binding strap used in connection with a SpO2 sensor comprises two clamping portions each of which is provided with an access opening for passing the light emitting portion or light receiving portion of the SpO2 sensor and a holding recess for holding corresponding light emitting portion or light receiving portion, wherein said access openings are designed to allow corresponding light emitting portion or light receiving portion to pass only when said access openings are undergoing a certain amount of deformation. The binding strap of the present invention is advantageous in that the light emitting portion and the light receiving portion of the SpO2 sensor might be tightly secured to the binding strap, and the lost of the binding strap when not use is ensured to be hard.

18 Claims, 7 Drawing Sheets

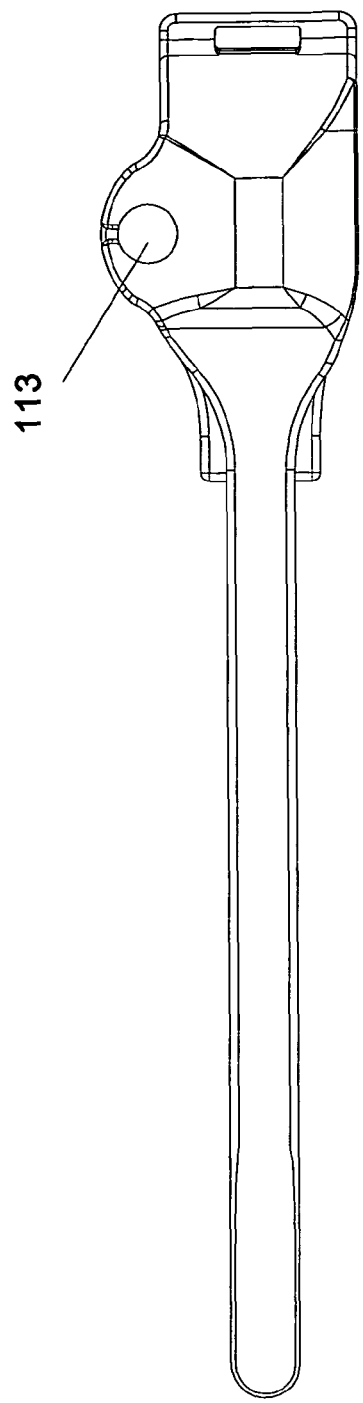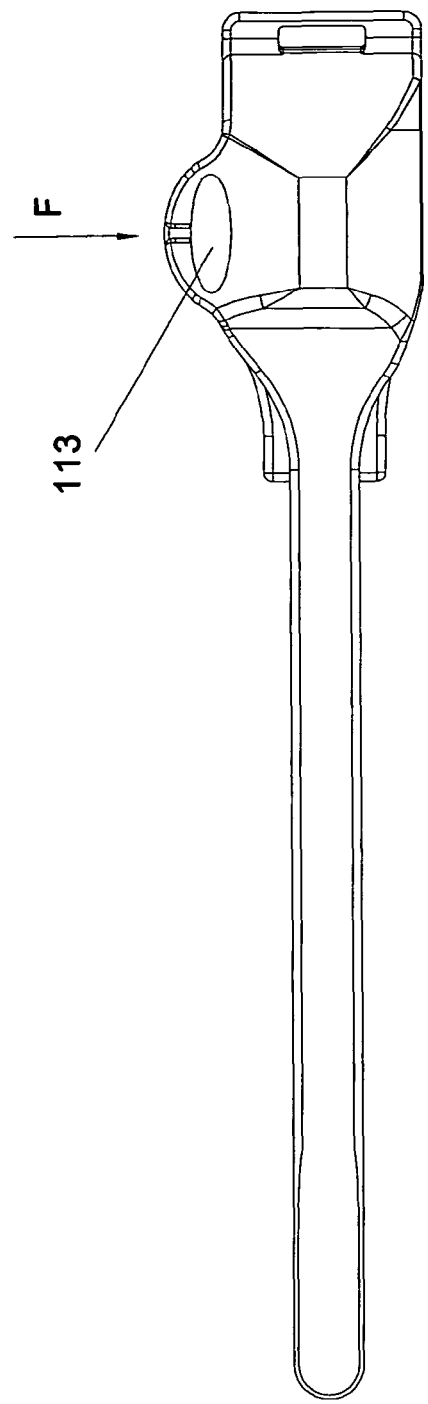
FIG.7A
FIG.7B

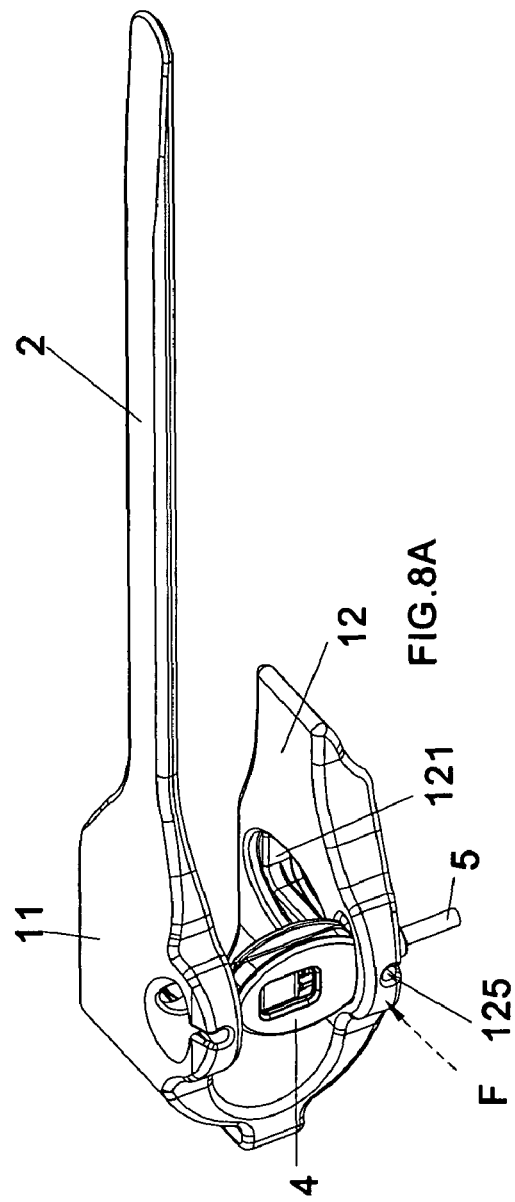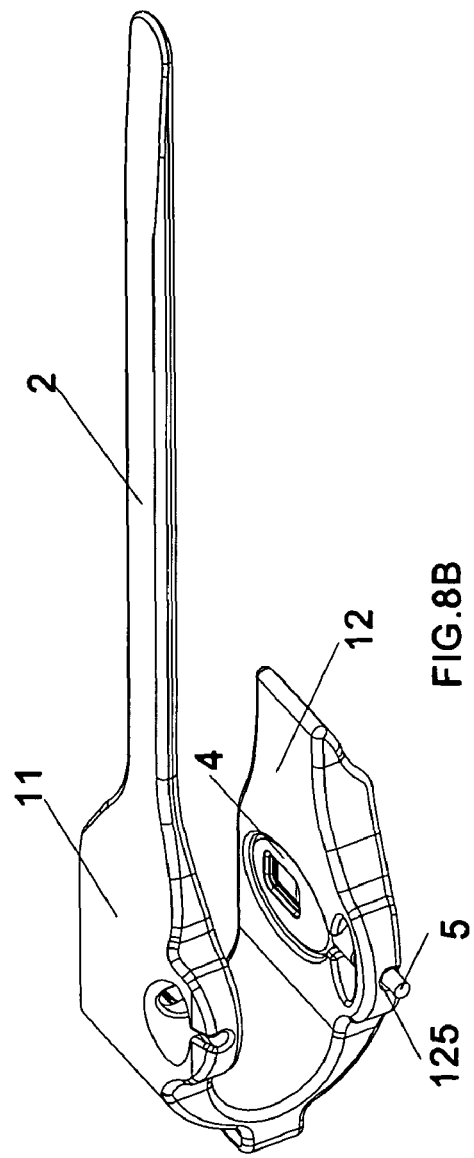

BINDING STRAP USED IN CONNECTION WITH SPO2 SENSOR

FIELD OF THE INVENTION

The present invention relates to a binding strap for medical use, in particular, to a binding strap used in connection with a SpO2 sensor.

BACKGROUND OF THE INVENTION

Generally, a SpO2 sensor is used to determine a saturation level of oxygen in blood, by means of a light emitting portion and a light receiving portion thereof which are to be fixed to a suitable position of a user, such as fingers, during the whole determination process. At this point, the SpO2 sensor is usually used in connection with an accessory which can hold the light emitting portion and the corresponding light receiving portion and also could secure said portions to the desired position. A binding strap may be the most commonly used form of the accessory, which may be provided with mounting formations capable of holding the light emitting portion and the light receiving portion of the SpO2 sensor therein, and which could be wound around the application position together with the light emitting portion and the light receiving portion. However, the conventional binding strap has a shortcoming in that the binding strap is liable to be lost due to carelessness of the user when the binding strap is temporarily not in use and meanwhile the light emitting portion and the light receiving portion are detached from respective mounting formations. In addition, fixing the binding strap onto a desired position is usually performed by winding an elongated wrapping body of the binding strap around a U-shaped main body of the binding strap. Unfortunately, the current mounting manner usually results in looseness of the binding strap.

SUMMARY OF THE INVENTION

Therefore, an object of the present invention is to provide a binding strap used in connection with a SpO2 sensor, which could reliably secure the light emitting portion and the light receiving portion of the SpO2 sensor and is also hard to be lost when not in use.

Another object of the present invention is to provide a binding strap which is hard to be loose in use.

According to the present invention, there is provided a binding strap used in connection with a SpO2 sensor, which comprises: a main body consisting of a first clamping portion, a second clamping portion and a connection portion connecting said first clamping portion and said second clamping portion; a wrapping body integrally extended from said first clamping portion of said main body; a first access opening penetratingly formed in said first clamping portion and allowing a light emitting portion of said SpO2 sensor to selectively pass therethrough; a first holding recess concavely formed in an inner side of said first clamping portion facing said second clamping portion, and adapted to hold said light emitting portion having passed through said first access opening; a second access opening penetratingly formed in said second clamping portion and allowing a light receiving portion of said SpO2 sensor to selectively pass therethrough; and a second holding recess concavely formed in an inner side of said second clamping portion facing said first clamping portion, and adapted to hold said light receiving portion having passed through said second access opening; wherein each of said first and second access openings is designed to allow said light emitting portion or said light receiving portion to pass therethrough only when said access opening is undergoing a certain amount of deformation.

Preferably, said binding strap is made of elastically deformable material.

Preferably, said elastically deformable material is silica gel.

Preferably, each of said light emitting portion and said light receiving portion is a plate member in an elliptical shape, said first access opening having an elliptical profile with a major axis slightly shorter than a minor axis of said light emitting portion, said second access opening having an elliptical profile with a major axis slightly shorter than a minor axis of said light receiving portion.

Preferably, each of said light emitting portion and said light receiving portion is a plate member in an elliptical shape, said first access opening having a circular profile with a diameter slightly shorter than a minor axis of said light emitting portion, said second access opening having a circular profile with a diameter slightly shorter than a minor axis of said light receiving portion.

Preferably, each of said light emitting portion and said light receiving portion is a plate member in an elliptical shape, and said first holding recess and said second holding recess are respectively formed in an elliptical shape with a slightly smaller dimension than that of corresponding light emitting portion or light receiving portion so as to tightly hold said light emitting portion or said light receiving portion therein.

Preferably, said first access opening and said second access opening respectively have an elliptical profile whose major axis is slightly shorter than a minor axis of corresponding light emitting portion or light receiving portion, and the minor axis of said first access opening and the major axis of said first holding recess lie in a common line, and the minor axis of said second access opening and the major axis of said second holding recess lie in another common line.

Preferably, said first clamping portion is provided with a first projection and said second clamping portion is provided with a second projection, both projections protruding in a width direction of said binding strap, and said first and second access openings are respectively formed in said first and second projections.

Preferably, said first clamping portion is further provided with a first inner cable clamping groove on said inner side thereof, which communicates said first access opening with said first holding recess, so as to clamp the cable or cable sheath of said light emitting portion therein from the inner side of said first clamping portion; and said second clamping portion is further provided with a second inner cable clamping groove on said inner side thereof, which communicates said second access opening with said second holding recess, so as to clamp the cable or cable sheath of said light receiving portion therein from the inner side of said second clamping portion.

Preferably, said first clamping portion is further provided with a first outer cable clamping groove on an outer side of said first clamping portion facing away from said second clamping portion, which is communicated with said first access opening and extends to an edge of said first clamping portion, so as to clamp the cable or cable sheath of said light emitting portion therein from the outer side of said first clamping portion; and said second clamping portion is further provided with a second inner cable clamping groove on an outer side of said second clamping portion facing away from said first clamping portion, which is communicated with said second access opening and extends to an edge of said second clamping portion, so as to clamp the cable or cable sheath of said light receiving portion therein from the outer side of said second clamping portion.

Preferably, said main body is in a substantially U-shape.

Preferably, said second clamping portion is further provided with a first inserting slot on an outer side of said second clamping portion facing away from said first clamping portion, which is positioned on a winding track of said wrapping body and is dimensioned so as to enable said wrapping body to pass through it and to be clamped therein.

Preferably, said first inserting slot is a cutout defined by a bottom wall, two side walls, and a beam portion bridging across said two side walls, in which a distance between said two side walls is substantially equal to a width of said wrapping body, and a spacing of bottom surface of said beam portion from the bottom wall of said first inserting slot is slightly smaller than a thickness of said wrapping body so as to clamp said wrapping body therein.

Preferably, said connection portion is provided with a second inserting slot on an outer side thereof, which is positioned on the winding track of said wrapping body and is dimensioned so as to enable said wrapping body to pass through it and to be clamped therein.

The binding strap of the present invention is advantageous in that the light emitting portion and the light receiving portion of the SpO2 sensor might be tightly secured to the binding strap, and in that suitably designed first and second access openings ensure a coupling between the light emitting portion and the light receiving portion and the binding strap, thus even if the binding strap is separated with the light emitting portion and the light receiving portion, the binding strap is hard to be lost. Furthermore, since the end portion of the wrapping body could be inserted into the first inserting slot as well as the second slot (if necessary), the position of the light emitting portion and the light receiving portion will not be easily shifted.

BRIEF DESCRIPTION OF DRAWINGS

FIG. 7A illustrates a state of a circular access opening before a certain amount of deformation is caused;

FIG. 7B illustrates another state of the circular access opening after a certain amount of deformation is caused.

DETAILED DESCRIPTION OF PREFERRED EMBODIMENTS

Figure 1:
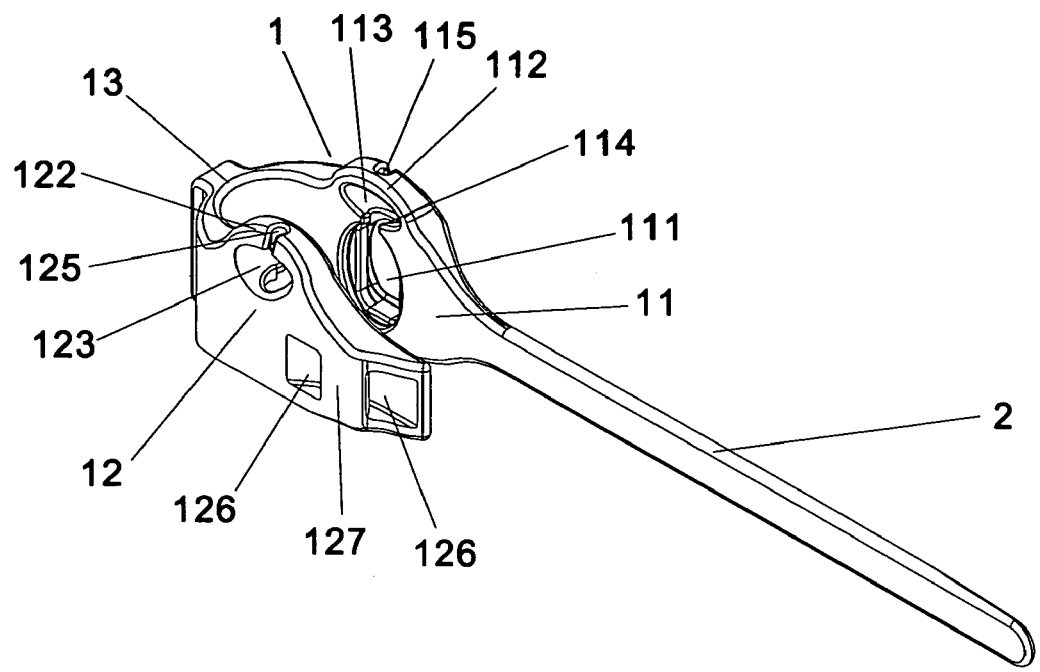
FIG. 1 to FIG. 3 are respectively three perspective views of the binding strap according to the present invention.
Figure 2:
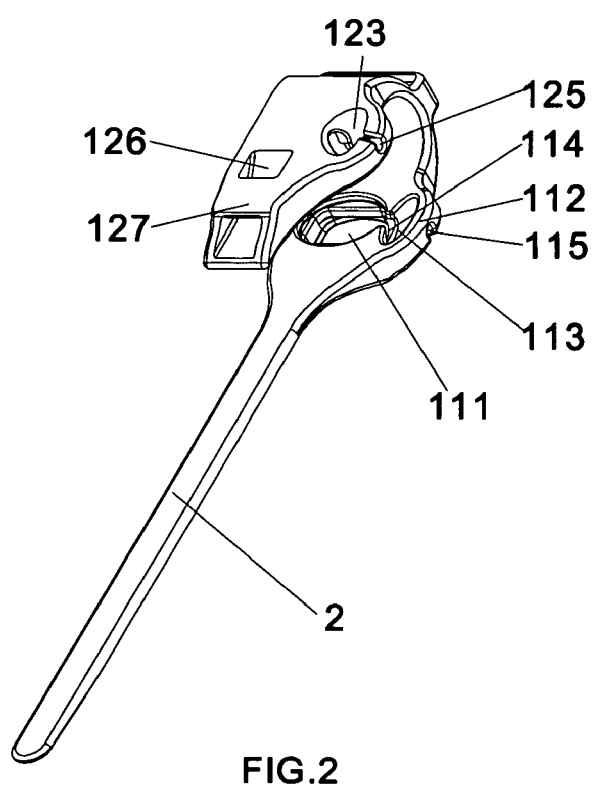
Figure 3:
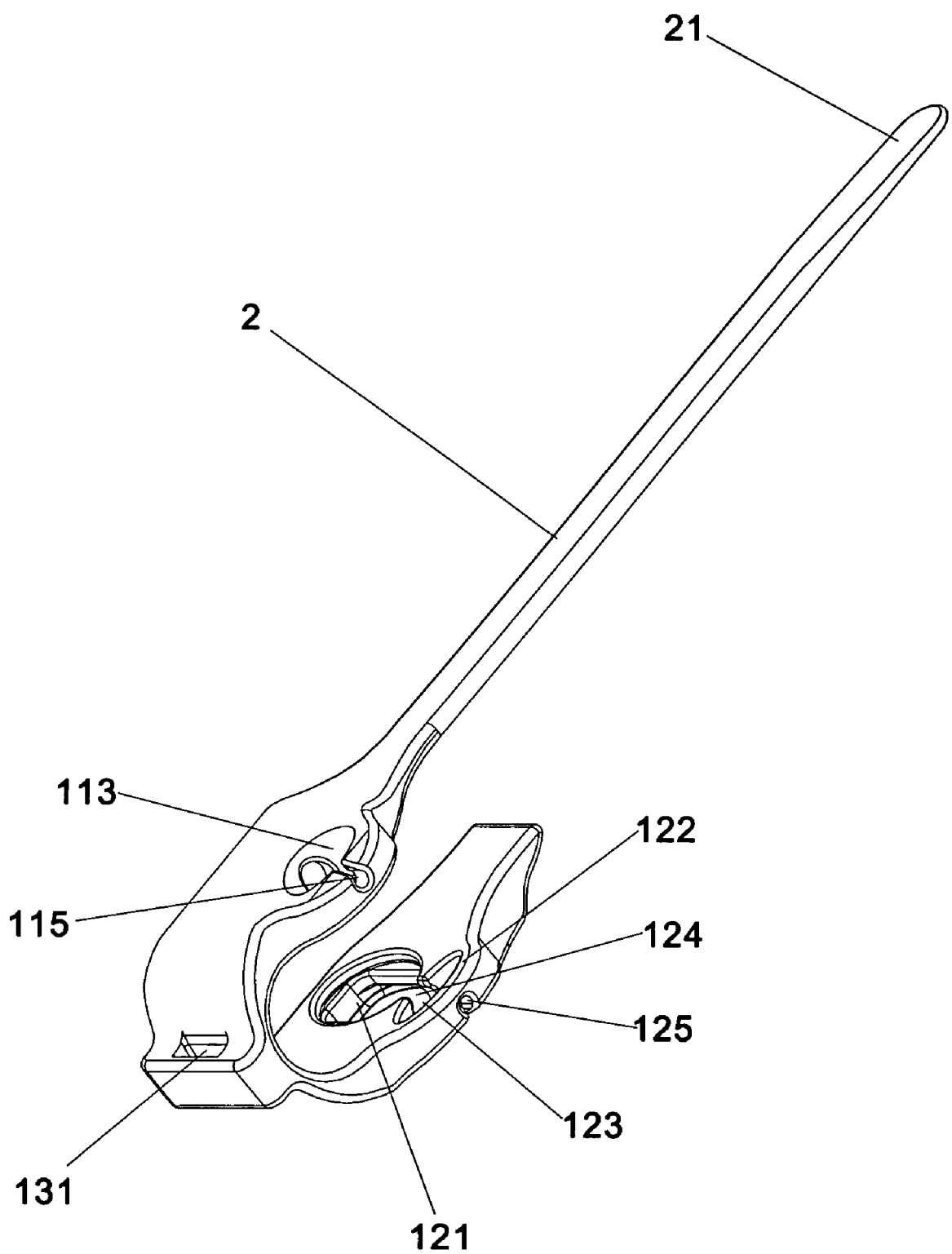
Figure 4:
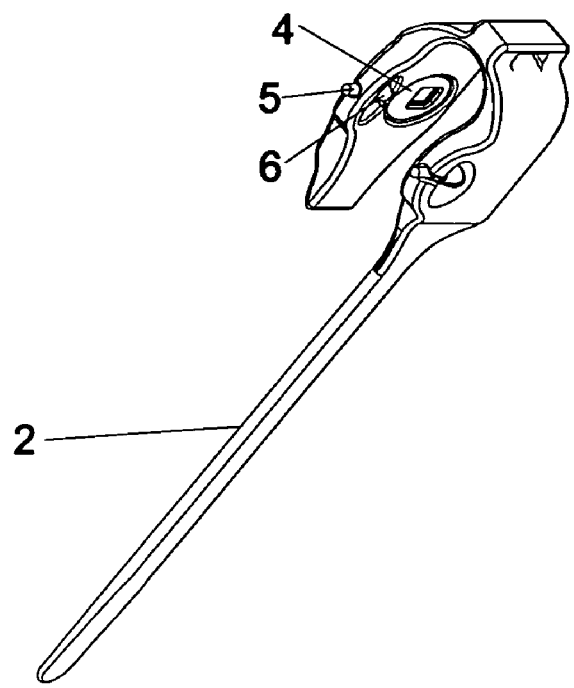
FIG. 4 is a perspective view of the binding strap according to the present invention with the light emitting portion and the light receiving portion of the SpO2 sensor mounted.
Figure 5:
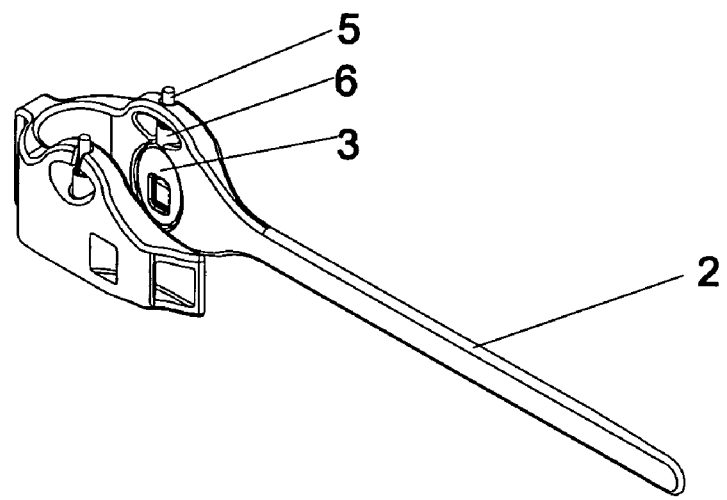
FIG. 5 is another perspective view of the binding strap according to the present invention with the light emitting portion and the light receiving portion of the SpO2 sensor mounted.

Hereinafter, the binding strap according to the present invention will be described with reference to the drawings.

Referring now to FIGS. 1 to 5, the binding strap includes: a main body 1 in a substantially U-shape consisting of a first clamping portion 11, a second clamping portion 12, and an arc-shaped connection part 13 connecting the first clamping portion 11 and the second portions 12; and a wrapping body 2 in the shape of an elongated strip integrally extended from the first clamping portion 11. The binding strap may be made of elastically deformable materials such as silica gel. The SpO2 sensor includes a light emitting portion 3, a light receiving portion 4, and cables 5 connected with the light emitting portion and the light receiving portion. Generally, each of the light emitting portion and the light receiving portion has an elliptical shape. The binding strap of the present invention is designed to accommodate the light emitting portion and the light receiving portion of the SpO2 sensor and also fix said portions to desired positions of the user.

Now the first clamping portion 11 of the main body 1 will be described in detail.

The first clamping portion 11 is provided with a first holding recess 111, a first access opening 113 and corresponding cable clamping grooves.

The first holding recess 111 is concavely formed in an inner side of the first clamping portion 11, i.e., the side of the first clamping portion 11 facing the second clamping portion 12, and has a profile matching that of the light emitting portion 3 so as to hold the light emitting portion 3. For example, in the case that the light emitting portion 3 is in an elliptical shape, the first holding recess 111 is preferably in the shape of a slightly smaller ellipse so as to tightly hold the light emitting portion 3 therein.

The first access opening 113 is penetratingly formed in the first clamping portion 11 and is designed to allow the light emitting portion 3 to selectively pass therethrough. Preferably, the first access opening 113 is penetratingly formed in a first projection 112 protruding from the first clamping portion 11 in the width direction of the binding strap 11. In the case that the light emitting portion 3 has an elliptical profile, the first access opening 113 may be in the shape of an ellipse which has a major axis slightly shorter than the minor axis of the light emitting portion 3, and the reason for that will be described hereinafter. In addition, in the case that both the first access opening 113 and the first holding recess 111 have an elliptical profile, preferably, the minor axis of the first access opening 113 and the major axis of the first holding recess 111 lie in a common line, as shown in the drawings.

The cable clamping grooves of the first clamping portion 11 are adapted to clamp the cable 5 or cable sheath 6 of the light emitting portion 3, which include a first inner cable clamping groove 114 provided at a side of the first clamping portion 11 facing the second clamping portion 12, i.e. the inner side of the first clamping portion 11, and a first outer cable clamping groove 115 provided at another side of the first clamping portion 11 facing away from the second clamping portion 12, i.e. an outer side of the first clamping portion 11. The first inner cable clamping groove 114 communicates the first holding recess 111 with the first access opening 113, thereby providing a passageway therebetween, so as to clamp the cable or cable sheath of the light emitting portion 3 therein at the inner side of the first clamping portion 11. The first outer cable clamping groove 115 is communicated with the first access opening 113 and extends to an edge of the first clamping portion 11 so as to clamp the cable or cable sheath of the light emitting portion 3 therein at the outer side of the first clamping portion 11.

Now the second clamping portion 12 of the main body 1 will be described in detail. It should be noted that the structure of the second clamping portion 12 is similar to that of the first clamping portion 11.

The second clamping portion 12 is provided with a second holding recess 121, a second access opening 123 and corresponding cable clamping grooves.

The second holding recess 121 is concavely formed in an inner side of the second clamping portion 12, i.e. the side of the second clamping portion 12 facing the first clamping portion 11, and has a profile matching that of the light receiving portion 4 so as to hold the light receiving portion 4. For example, in the case that the light receiving portion 4 is in an elliptical shape, the second holding recess 121 is preferably in a slightly smaller ellipse so as to tightly hold the light receiving portion 4 therein.

The second access opening 123 is penetratingly formed in the second clamping portion 12 and is designed to allow the light receiving portion 4 to selectively pass therethrough. Preferably, the second access opening 123 is penetratingly formed in a second projection 122 protruding from the second clamping portion 12 in the width direction of the binding strap 11. In the case that the light receiving portion 4 has an elliptical profile, the second access opening 123 may be in the shape of an ellipse which has a major axis slightly shorter than the minor axis of the light receiving portion 4, and the reason for that will be described hereinafter. In addition, in the case that both the second access opening 123 and the second holding recess 121 have an elliptical profile, preferably, the minor axis of the second access opening 123 and the major axis of the second holding recess 121 lie in a common line, as shown in the drawings.

The cable clamping grooves of the second clamping portion 12 are adapted to clamp the cable 5 or cable sheath 6 of the light receiving portion 4, which include a second inner cable clamping groove 124 provided at an inner side of the second clamping portion 12, i.e. the side of the second clamping portion 12 facing the first clamping portion 11, and a second outer cable clamping groove 125 provided at an outer side of the second clamping portion 12, i.e. the side of the second clamping portion 12 facing away from the first clamping portion 11. The second inner cable clamping groove 124 communicates the second holding recess 121 with the second access opening 123, thereby providing a passageway therebetween, so as to clamp the cable or cable sheath of the light receiving portion 4 therein at the inner side of the second clamping portion 12. The second outer cable clamping groove 125 is communicated with the second access opening 123 and extends to an edge of the second clamping portion 12 so as to clamp the cable or cable sheath of the light receiving portion 4 therein at the outer side of the second clamping portion 12.

Besides the above mentioned portions similar to those of the first clamping portion 11, the second clamping portion 12 is further provided with a first inserting slot 126 on the outer side thereof, which is positioned on the winding track of the wrapping body 2 and is suitably dimensioned so as to enable the wrapping body 2 to pass through it and meanwhile to be suitably clamped therein. In the illustrative preferred embodiment, the first inserting slot 126 is generally a cutout defined by a bottom wall, two side walls, and a beam portion 127 bridging across the two side walls, in which a distance between the two side walls is substantially equal to a width of the wrapping body 2, and a spacing of the bottom surface of the beam portion 127 from the bottom wall of the first inserting slot 126 is slightly smaller than a thickness of the wrapping body 2 so as to suitably clamp the wrapping body 2 therein.

The connection portion 13 is further provided with a second inserting slot 131 on the outer side thereof, which is also positioned on the winding track of the wrapping body 2 and is suitably dimensioned so as to enable the wrapping body 2 to pass through it and to be suitably clamped therein, if necessary.

In the present invention, each of the first and second holding recesses has a profile matching that of corresponding light emitting portion or light receiving portion, and the size of each holding recess is slightly smaller than that of corresponding light emitting portion or light receiving portion so as to tightly hold corresponding portion therein.

Figure 6A:
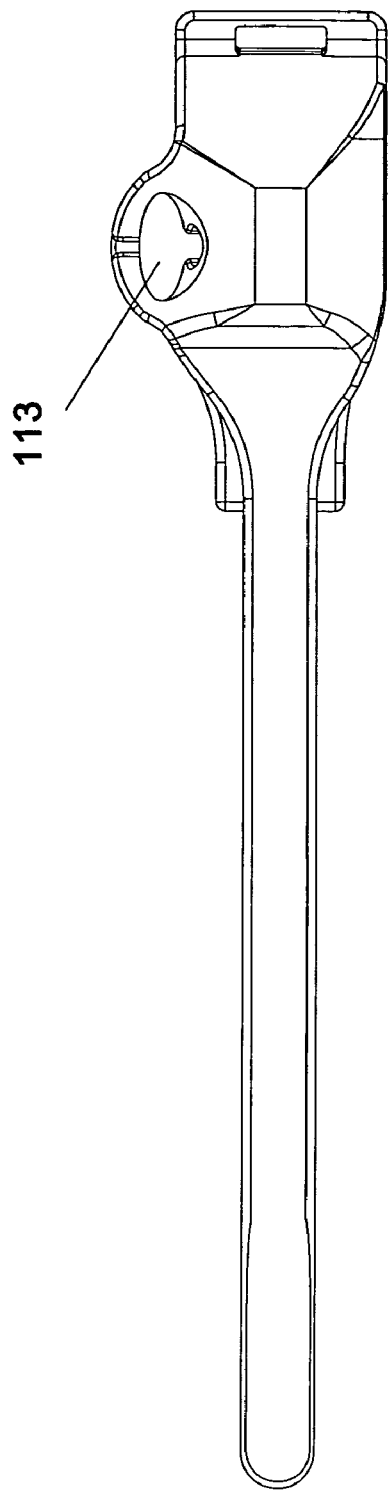
FIG. 6A illustrates an original state of an elliptical access opening before a certain amount of deformation is caused.
Figure 6B:
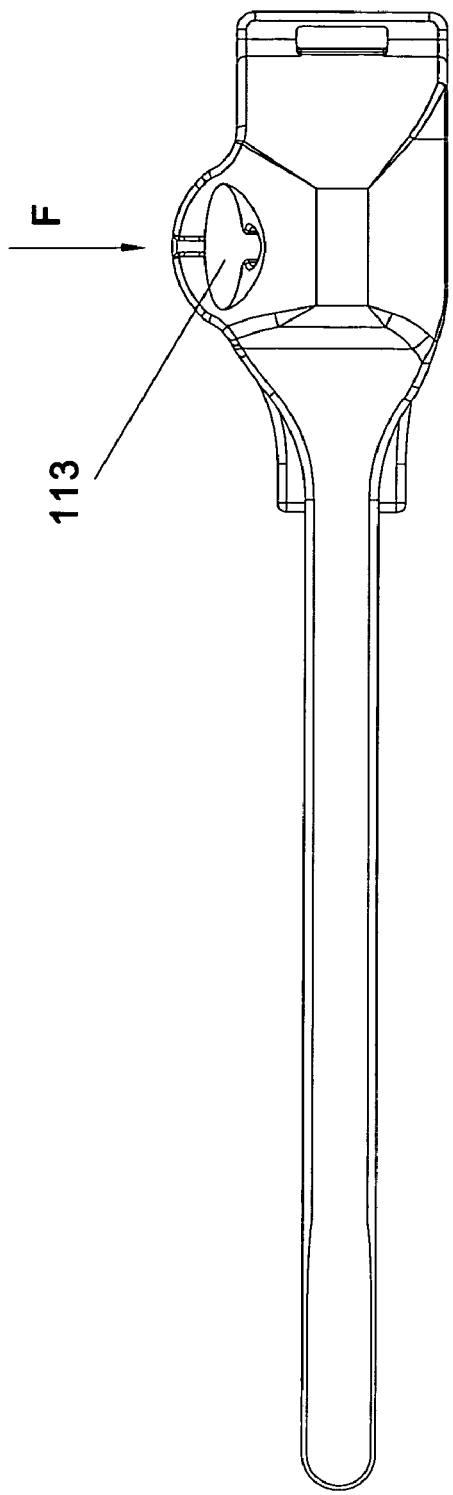
FIG. 6B illustrates another state of the elliptical access opening after a certain amount of deformation is caused.
Figure 8C:
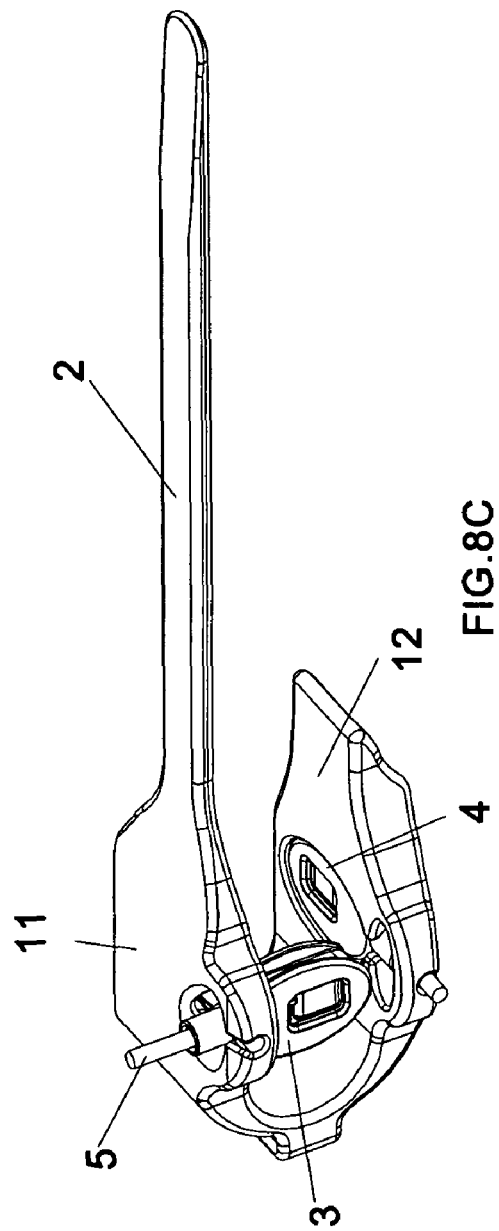
FIGS. 8A-8B illustrate several steps during a process of mounting the light emitting portion and the light receiving portion of the SpO2 sensor onto the binding strap according to the present invention.
Figure 8D:
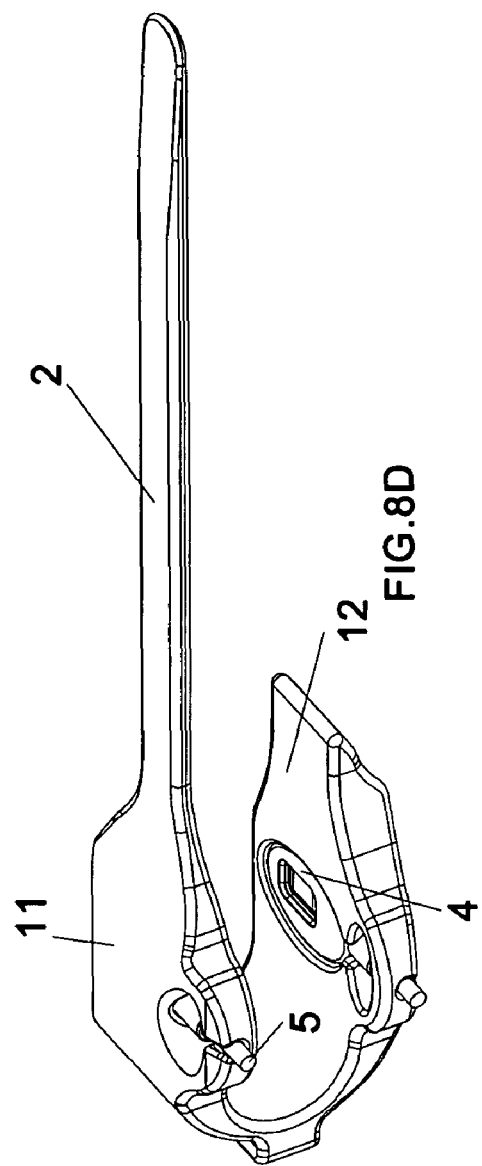

As to the first and second access openings, they are suitably dimensioned so that the light emitting portion or the light receiving portion of the SpO2 sensor can not pass through corresponding access opening when the access opening is in an unforced state unless the access opening is forced to undergo a certain amount of deformation. In other words, the access openings allow the light emitting portion and the light receiving portion to selectively pass therethrough. For example, in the case that the light emitting portion and the light receiving portion are both identical elliptical plate member, the first and second access openings may be in the shape of an ellipse with a major axis slightly shorter than the minor axis of the light emitting portion or the light receiving portion, such that the ellipse profile of the access opening can prevent the light emitting portion or the light receiving portion from passing therethrough under its unforced state, as shown in FIG. 6A, and such that the ellipse profile of the access opening will allow the light emitting portion or the light receiving portion to pass therethrough when the access opening undergoes a force so that the minor axis becomes shorter and the major axis becomes longer, as shown in FIG. 6B. For elliptical light emitting portion and light receiving portion, alternatively, the first and second access openings may be in the shape of a circle with a diameter slightly shorter than the minor axis of the light emitting portion or the light receiving portion such that the circular profile of the access opening can prevent the light emitting portion or the light receiving portion from passing therethrough under its unforced state, as shown in FIG. 7A, and such that the circular profile of the access opening will allow the light emitting portion or the light receiving portion to pass therethrough when the access opening undergoes a force so that the circular profile thereof becomes a substantially elliptical profile, as shown in FIG. 7B. It should be understood from the above spirit that access openings with various profiles could be used, as long as the profiles allow the light emitting portion and the light receiving portion to selectively pass therethrough.

The size of each of the cable clamping grooves may be slightly smaller than that of corresponding cable or cable sheath so as to clamp the cable or cable sheath.

A method of mounting the light emitting portion and the light receiving portion of the SpO2 sensor onto the binding strap of the present invention will be described with reference to FIGS. 8A-8D.

FIGS. 8A-8D illustrate several steps of a mounting process in which the light receiving portion 4 is firstly mounted and then the light emitting portion 3 is mounted. As shown in the drawings, in order to mount the light emitting portion and the light receiving portion of the SpO2 sensor, firstly, a certain force F may be applied to the top of the second access opening 123 to achieve a flattened profile to allow the light receiving portion 4 to pass therethrough. After the light receiving portion 4 completely passes through the second access opening 123, the force applied to the top of the second access opening 123 could be released so as to allow the second access opening 123 to restore its initial shape. Then, the light receiving portion 4 may be pressed and fixed into the second holding recess 121. The cable 5 and the cable sheath 6 might be respectively pressed into the second outer cable clamping groove 125 and the second inner cable clamping groove 124. Similarly, the light emitting portion 3 could be mounted onto the first clamping portion 11.

In use, the U-shaped main body 1 is firstly clamped over a suitable location of the user, such as the foot or the hand. Then the wrapping body 2 is wound around the location with the end portion 21 of the wrapping body 2 inserted into the first inserting slot 126 of the second clamping portion 12. Then the wrapping body 2 is clamped by means of, for example, the friction between the wrapping body 2 and the first inserting slot 126. For those users with smaller body figures, since a required effective length of the wrapping body is shorter, the end portion of the wrapping body could be both inserted through the first inserting slot 126 and the second inserting slot 131.

Thus, if any of the light emitting portion and the light receiving portion is detached from corresponding holding recess, unless the corresponding access opening is purposely again pressed to produce deformation, the light emitting portion or the light receiving portion may not exit the access opening since the access opening is in an unforced state. Therefore, the binding strap could not be completely separated from the light emitting portion and the light receiving portion, and then the lost of the binding strap could be prevented.

The binding strap of the present invention is advantageous in that the light emitting portion and the light receiving portion of the SpO2 sensor might be tightly secured to the binding strap, and that the light emitting portion and the light receiving portion could not be easily detached from the binding strap. Further, suitably designed first and second access openings ensure a coupling between the light emitting portion and the light receiving portion and the binding strap. That is, even if the binding strap is separated with the light emitting portion and the light receiving portion, the binding strap is to be hanged from the cable of the SpO2 sensor and is hard to be lost. Furthermore, since the end portion of the wrapping body could be inserted into the first inserting slot as well as the second slot (if necessary), the position of the light emitting portion and the light receiving portion is not easily shifted.

It should be obvious that changes to certain details of the preferred embodiment can be made without departing from the spirit and scope of the invention defined in the appended claims.

What is claimed is:

1. A binding strap used in connection with a SpO2 sensor, which comprises:
   a main body consisting of a first clamping portion, a second clamping portion and a connection portion connecting said first clamping portion and said second clamping portion, wherein the first clamping portion defines an inner side that faces toward the second clamping portion and an outer side that faces away from the second clamping portion, and wherein the second clamping portion defines an inner side that faces toward the first clamping portion and an outer side that faces away from the second clamping portion;
   a wrapping body integrally extended from said first clamping portion of said main body;
   a first access opening extending through the outer side and the inner side of the first clamping portion and configured to allow a light emitting portion of said SpO2 sensor to selectively pass therethrough;
   a first holding recess concavely formed in the inner side of said first clamping portion, wherein the first holding recess is configured to hold said light emitting portion after the light emitting portion has passed through said first access opening;
   a second access opening extending through the outer side and the inner side of the second clamping portion and configured to allow a light receiving portion of said SpO2 sensor to selectively pass therethrough; and
   a second holding recess concavely formed in the inner side of said second clamping portion, wherein the second holding recess is configured to hold said light receiving portion after the light receiving portion has passed through said second access opening;
   wherein each of said first and second access openings is configured to allow said light emitting portion or said light receiving portion, respectively, to pass therethrough only when said access opening is undergoing deformation.

2. The binding strap according to claim 1, wherein said binding strap is made of elastically deformable material.

3. The binding strap according to claim 2, wherein said elastically deformable material is silica gel.

4. The binding strap according to claim 1, wherein each of said light emitting portion and said light receiving portion is a plate member in an elliptical shape, said first access opening having an elliptical profile with a major axis slightly shorter than a minor axis of said light emitting portion, said second access opening having an elliptical profile with a major axis slightly shorter than a minor axis of said light receiving portion.

5. The binding strap according to claim 1, wherein each of said light emitting portion and said light receiving portion is a plate member in an elliptical shape, said first access opening having a circular profile with a diameter slightly shorter than a minor axis of said light emitting portion, said second access opening having a circular profile with a diameter slightly shorter than a minor axis of said light receiving portion.

6. The binding strap according to claim 1, wherein each of said light emitting portion and said light receiving portion is a plate member in an elliptical shape, and said first holding recess and said second holding recess are respectively formed in an elliptical shape with a slightly smaller dimension than that of corresponding light emitting portion or light receiving portion so as to tightly hold said light emitting portion or said light receiving portion therein.

7. The binding strap according to claim 6, wherein said first access opening and said second access opening respectively have an elliptical profile whose major axis is slightly shorter than a minor axis of corresponding light emitting portion or light receiving portion, and the minor axis of said first access opening and the major axis of said first holding recess lie in a common line, and the minor axis of said second access opening and the major axis of said second holding recess lie in another common line.

8. The binding strap according to claim 1, wherein said first clamping portion is provided with a first projection and said second clamping portion is provided with a second projection, both projections protruding in a width direction of said binding strap, and said first and second access openings are respectively formed in said first and second projections.

9. The binding strap according to claim 1, wherein
wherein said first clamping portion is further provided with a first inner cable clamping groove on said inner side thereof, which communicates said first access opening with said first holding recess, so as to clamp the cable or cable sheath of said light emitting portion therein from the inner side of said first clamping portion; and
wherein said second clamping portion is further provided with a second inner cable clamping groove on said inner side thereof, which communicates said second access opening with said second holding recess, so as to clamp the cable or cable sheath of said light receiving portion therein from the inner side of said second clamping portion.

10. The binding strap according to claim 1, wherein
said first clamping portion is further provided with a first outer cable clamping groove on an outer side of said first clamping portion facing away from said second clamping portion, which is communicated with said first access opening and extends to an edge of said first clamping portion, so as to clamp the cable or cable sheath of said light emitting portion therein from the outer side of said first clamping portion; and
said second clamping portion is further provided with a second outer cable clamping groove on an outer side of said second clamping portion facing away from said first clamping portion, which is communicated with said second access opening and extends to an edge of said second clamping portion, so as to clamp the cable or cable sheath of said light receiving portion therein from the outer side of said second clamping portion.

11. The binding strap according to claim 1, wherein said main body is in a substantially U-shape.

12. The binding strap according to claim 1, wherein said second clamping portion is further provided with a first inserting slot on an outer side of said second clamping portion facing away from said first clamping portion, which is positioned on a winding track of said wrapping body and is dimensioned so as to enable said wrapping body to pass through it and to be clamped therein.

13. The binding strap according to claim 12, wherein said first inserting slot is a cutout defined by a bottom wall, two side walls, and a beam portion bridging across said two side walls, in which a distance between said two side walls is substantially equal to a width of said wrapping body, and a spacing of bottom surface of said beam portion from the bottom wall of said first inserting slot is slightly smaller than a thickness of said wrapping body so as to clamp said wrapping body therein.

14. The binding strap according to claim 12, wherein said connection portion is provided with a second inserting slot on an outer side thereof, which is positioned on the winding track of said wrapping body and is dimensioned so as to enable said wrapping body to pass through it and to be clamped therein.

15. The binding strap according to claim 1, wherein the first clamping portion further comprises a side edge that extends between the inner and outer sides, wherein the second portion further comprises a side edge that extends between the inner and outer sides, and wherein each of said first and second access openings is configured to allow said light emitting portion or said light receiving portion, respectively, to pass therethrough only when said access opening is being deformed due to application of force to the side edge of the first or second clamping portion, respectively.

16. A binding strap used in connection with a SpO2 sensor, which comprises:
a main body consisting of a first clamping portion, a second clamping portion and a connection portion connecting said first clamping portion and said second clamping portion;
a wrapping body integrally extended from said first clamping portion of said main body;
a first access opening penetratingly formed in said first clamping portion and configured to allow a light emitting portion of said SpO2 sensor to selectively pass therethrough;
a first holding recess concavely formed in an inner side of said first clamping portion facing said second clamping portion, wherein the first holding recess is configured to hold said light emitting portion after the light emitting portion has passed through said first access opening;
a second access opening penetratingly formed in said second clamping portion and configured to allow a light receiving portion of said SpO2 sensor to selectively pass therethrough; and
a second holding recess concavely formed in an inner side of said second clamping portion facing said first clamping portion, wherein the second holding recess is configured to hold said light receiving portion after the light receiving portion has passed through said second access opening;
wherein each of said first and second access openings is designed to allow said light emitting portion or said light receiving portion, respectively, to pass therethrough only when said access opening is undergoing deformation; and
wherein said first clamping portion is provided with a first projection and said second clamping portion is provided with a second projection, both projections protruding in a width direction of said binding strap, and said first and second access openings are respectively formed in said first and second projections.

17. A binding strap used in connection with a SpO2 sensor, which comprises:
a main body consisting of a first clamping portion, a second clamping portion and a connection portion connecting said first clamping portion and said second clamping portion;
a wrapping body integrally extended from said first clamping portion of said main body;
a first access opening penetratingly formed in said first clamping portion and configured to allow a light emitting portion of said SpO2 sensor to selectively pass therethrough;
a first holding recess concavely formed in an inner side of said first clamping portion facing said second clamping portion, wherein the first holding recess is configured to hold said light emitting portion after the light emitting portion has passed through said first access opening;
a second access opening penetratingly formed in said second clamping portion and configured to allow a light receiving portion of said SpO2 sensor to selectively pass therethrough; and
a second holding recess concavely formed in an inner side of said second clamping portion facing said first clamping portion, wherein the second holding recess is configured to hold said light receiving portion after the light receiving portion has passed through said second access opening;
wherein each of said first and second access openings is designed to allow said light emitting portion or said light receiving portion, respectively, to pass therethrough only when said access opening is undergoing deformation;

wherein said first clamping portion is further provided with a first inner cable clamping groove on said inner side thereof, which communicates said first access opening with said first holding recess, so as to clamp the cable or cable sheath of said light emitting portion therein from the inner side of said first clamping portion; and wherein said second clamping portion is further provided with a second inner cable clamping groove on said inner side thereof, which communicates said second access opening with said second holding recess, so as to clamp the cable or cable sheath of said light receiving portion therein from the inner side of said second clamping portion.

18. A binding strap used in connection with a SpO2 sensor, which comprises:

a main body consisting of a first clamping portion, a second clamping portion and a connection portion connecting said first clamping portion and said second clamping portion;

a wrapping body integrally extended from said first clamping portion of said main body;

a first access opening penetratingly formed in said first clamping portion and configured to allow a light emitting portion of said SpO2 sensor to selectively pass therethrough;

a first holding recess concavely formed in an inner side of said first clamping portion facing said second clamping portion, wherein the first holding recess is configured to hold said light emitting portion after the light emitting portion has passed through said first access opening;

a second access opening penetratingly formed in said second clamping portion and configured to allow a light receiving portion of said SpO2 sensor to selectively pass therethrough; and a second holding recess concavely formed in an inner side of said second clamping portion facing said first clamping portion, wherein the second holding recess is configured to hold said light receiving portion after the light receiving portion has passed through said second access opening;

wherein each of said first and second access openings is designed to allow said light emitting portion or said light receiving portion, respectively, to pass therethrough only when said access opening is undergoing deformation;

wherein said first clamping portion is further provided with a first outer cable clamping groove on an outer side of said first clamping portion facing away from said second clamping portion, which is communicated with said first access opening and extends to an edge of said first clamping portion, so as to clamp the cable or cable sheath of said light emitting portion therein from the outer side of said first clamping portion; and wherein said second clamping portion is further provided with a second outer cable clamping groove on an outer side of said second clamping portion facing away from said first clamping portion, which is communicated with said second access opening and extends to an edge of said second clamping portion, so as to clamp the cable or cable sheath of said light receiving portion therein from the outer side of said second clamping portion.

* * * * *